(12) United States Patent
Stalker et al.

(10) Patent No.: US 6,566,586 B1
(45) Date of Patent: May 20, 2003

(54) COTTON EXPANSIN PROMOTER SEQUENCE

(75) Inventors: David M. Stalker, Woodland, CA (US); Julie R. Pear, Davis, CA (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 09/004,056

(22) Filed: Jan. 7, 1998

Related U.S. Application Data

(60) Provisional application No. 60/034,914, filed on Jan. 7, 1997.

(51) Int. Cl.[7] .......................... A01H 5/00; C07H 21/04; C12N 5/14; C12N 15/82
(52) U.S. Cl. .................... 800/298; 435/320.1; 435/419; 536/24.1
(58) Field of Search ............................ 435/320.1, 419, 435/468; 536/24.1; 800/278, 298

(56) References Cited

U.S. PATENT DOCUMENTS

| | | |
|---|---|---|
| 5,004,863 A | 4/1991 | Agracetus |
| 5,495,070 A | 2/1996 | Agracetus |

FOREIGN PATENT DOCUMENTS

| | | |
|---|---|---|
| WO | WO 95/08914 | 4/1995 |
| WO | WO 96/35442 | 11/1996 |
| WO | WO 96/40924 | 12/1996 |
| WO | WO 96/40951 | 12/1996 |

OTHER PUBLICATIONS

Proc. Natl. Acad, Maliyakal, et al., Jul. 1, 1992, vol. 89:5769–5773.
Plant Cell Phys, Shimizu, et al. Aug. 20, 1997, vol. 38, 375–378.
Indian Soc Agril, Maliyakal, Aug. 20, 1993, 27–32.
Stam M, et al. "The silence of genes in transgenic plants." Ann. Bot. 79:3–12, 1997.*
Koziel MG, et al. "Optimizing expression of transgenes with an emphasis on post–transcriptional events." Plant Mol. Biol. 32: 393–405, 1996.*
Smith CJS, et al. "Antisense RNA inhibition of polygalacturonase gene expression in transgenic tomatoes." Nature 334: 724–726, Aug. 1988.*
Benfey PN, et al. "The cauliflower mosaic virus 35S promoter: Combinatorial regulation of transcription in plants." Science 250: 959–966, Nov. 1990.*
Kim Y, et al. "A 20 nucleotide upstream element is essential for the nopaline synthase (nos) promoter activity." Plant Mol. Biol. 24: 105–117, 1994.*

* cited by examiner

*Primary Examiner*—Amy J. Nelson
(74) *Attorney, Agent, or Firm*—Alissa Eagle

(57) ABSTRACT

Provided is a cotton (*Gossypium hirsutum*) promoter region from an expansin gene expressed in developing fiber.

4 Claims, 6 Drawing Sheets

```
         420             440             460             480
          *               *               *               *
AAAAAACTAAAAAATTAATATGAAAAAAATTGATAACCAACTAAATTATAATTAAAAGTTCAAAAAATTAAAAAA 500             520             540             560
          *               *               *               *
ATCCCGATTGAACCAGTATCACCCCTAAATTAGATGAGGCCATATATTTAACATATTAGAAAATGAAACTCTAGAAAAATAT
                                                              >XbaI 580             600             620             640
          *               *               *               *
ATAAAAGTAAATTTATTGGGCGAGAGATTAGACAAAGTCAATGCACCCCTCAATGAATAGATATTATTCCCAATGAAAGTT 660             680             700             720
          *               *               *               *
TCCGTTTTCCACCTCCTACCCAAAAACTCCAAAGTCTCCAGAGACGCGCCTGAATCGTGACTGGGTAGCCGGGGTACAT 740             760             780             800
          *               *               *               *
ACTACAACCCTAAATGCTTTATAGCGCATAGATCATGGGTTTAGCTTTGGATCCCATAAAGTACAAATACTGAGTTCTT
>BclI   >NsiI                                     >BamHI 820             840             860             880
          *               *               *               *
TAGTGAATGATCATGCATGGACACATGATGTCTCTTTTTAGGCATTGACAAACTCGTCATTTTTCATACAATTTCTTT 900             920             940             960
          *               *               *               *
```

FIGURE 1B

```
                *              *              *              *              *
GGTCAATTAATTTTCCATTAAATTAGGAAACCGCCCTCCAAAATTATATNTGGTAACGGTGGAAGGNTTATCCAANTTCG
     *              *              *              *              *
    980            1000           1020           1040

*              *              *              *              *
ACCATTCGAACCACTTTAAAAAATTAGAAAGTTATAATTTTTTTCAAAAAAACTATAATACCTCTCTAGTTTTAGCT
     *              *              *              *
    1060           1080           1100                           >BclI
                                                                  |
                                                                 1120
                *              *              *              *              *
AATTAAATTATTATTTATTTATTGTTATTAAAGTGTAACTTGCACTCAACTATTAGTAAGTTTACGTTTTG
     *              *              *              *              *
    1140           1160           1180           1200

*              *              *              *              *
ATCACTTAATTCAGAAAGTTAAAAAAATGGTCTCTTTGAACTATTCGAAAATTTCATTTAAGTTACTGGAATATTTAAAAG
     *              *              *              *              *
    1220           1240           1260           1280

*              *              *              *              *
TTTTTATTTAAGTCACCGGGCTATTAAGTTTTTTTTTTAAAAATTCGATTAGCAAGTTCCAAGCTACGATTCGATAAGTGA
     *              *              *              *              *
    1300           1320           1340           1360

*              *              *              *              *
TACAATGGATTTATACTTATTGACAAATAGAATATACATTAGGTCCAAGTTGATATTACGGTCAGTGTTGAAAATCGAAA
     *              *              *              *              *
    1380           1400           1420           1440

*              *              *              *
AAAAATATTTGGATTTGATTCATAAATTTATGACTTCAAAGCTGGTTCATGAAAAAGAACTAAAGTGTAGGAGGGAAGG
     *              *              *
    1460           1480           1500                           >SwaI
                                                                  |
                                                                 1520
```

FIGURE 1C

```
         *            *            *            *            *            *            *   |*
AAAAAAATATCTTTTGATTGGCACAAACAGTGCGAACAAAGAAGACCACACAATAACAATTTTAACAATATACTAATTTA
*            *            *            *            *            *            *            *
           1540         1560         1580         1600
                  >HpaI
                 ┌──┐

AATGAAAAATTTCAATAATTTAATAAGTTAACCGAGAGAAAACTTACTAAGAGTTAGTTACCCCCTGTTAAAATAACTTT
         *            *            *            *            *            *            *            *
           1620         1640         1660         1680

CATGAAGTAATAGAAACTTTTAGTACGTATCATCTTATATAGAACAATTCTATTTCAGGAAAGTCAAAGAAAATTGTAT
         *            *            *            *            *            *            *            *
           1700         1720         1740         1760

TGTAGAAAATGGCGAATTTTTTCACCTTTCAGTCCTTCCCTGATCGGCGCTTGTGAAAACGAAAAACCTGAGTCTGATT
         *            *            *            *            *            *            *            *
           1780         1800         1820         1840

GXXTGACTGAAAATGAACTTATCATCACCATTCACTATTACCAACTTCAAATGATAGGGAATTAACTGGTAAAGTGTAA
         *            *            *            *            *            *            *            *
           1860         1880         1900         1920
                                              >MunI
                                            ┌──┐

CTCCACCGATGGTTGAGGTGGTTGGCTGGAGTTAAATGAGATTTTTTTAGTTTTGTTTCAAGTGGCTTCAATTGCAAGCA
```

FIGURE 1D

```
                1940             1960             1980             2000
                  *                *                *                *
ATTAGGAGACTGCGCTGGAATAACCCCTCGCTCAACCTTCGCCATTGTTATGGTTTAATTAAACATTATGTTTCCATCC 2020             2040             2060             2080
                  *                *                *                *
ATCTATATATTTATATCCATTAAAACAAGTCGTTGAGCAAATAATGGATACTGGATACCATCATATCTATGATTAAAATTTT 2100             2120             2140             2160
                  *                *                *                *
GCATGTGCCCTTTAATGTATAGCTTAAGCCTTAATTATCCTCCAAATTTGTACTCTTTCACCACTTAATTAGCTACGTA 2180             2200             2220             2240
                  *                *                *                *
CGGTACTTAGCGTTGCTTGTCATCTTCTGTACTACAAACTCTTCTCATTTTGTATAAATAGCTATACACTTTTTCTCTC

>NheI
                  >MunI      >NheI
                2260     |   |  |   2300             2320
                  *      |   |  *     *                *
CTCAAATCAATAAGGTTAGGTCAGCCAATTGTTTGAGCTTAGCTAGCTCTTACTCAAATGGCAACCAAAACGATGATGTTG 2340             2360             2380             2400
                  *                *                *                *
CAAATATTTCCACTTTTCTCTTTTTGTTCAGTGTCTGCAACTCCATTTCCTTGGTGCTAATGGAGATGACAATGGTGG 2420             2440             2460             2480
                  *                *                *                *
TTGGCAAACTGCCCATGCCACCTTCTACGGTGGTGCTGATGCTACCGGCACAATGGGTGAGTTTCAAACTTTCAAACCAT 2500             2520             2540             2560
```

FIGURE 1E

```
                *         *         *         *         *         *         *
TACGGCATTACCTACATAAAAATCTCTAGGCTATGTTCTTAATTTGTGATGTTCTCTATAGGGGAGCTTGTGGTTATGG
         >EcoR1            >SpeI
         |   |             |
      2580              2600
         *   *             *         *
AAACCTGTACAGTCAAAGCCGAATTCCAGCACACTGGCGGCCGTTACTAGTGGA
```

FIGURE 1F

SEQUENCE LISTING

```
<160> NUMBER OF SEQ ID NOS: 1

<210> SEQ ID NO 1
<211> LENGTH: 2614
<212> TYPE: DNA
<213> ORGANISM: Gossypium hirsutum
<220> FEATURE:
<221> NAME/KEY: promoter
<222> LOCATION: (930)
<223> OTHER INFORMATION: unknown nucleotide
<220> FEATURE:
<221> NAME/KEY: promoter
<222> LOCATION: (947)
<223> OTHER INFORMATION: unknown nucleotide
<220> FEATURE:
<221> NAME/KEY: promoter
<222> LOCATION: (956)
<223> OTHER INFORMATION: unknown nucleotide

<400> SEQUENCE: 1
tacgactcac tatagggcga attgggccct ctagatgcat gctcgagcgg ccgccagtgt      60
gatggatatc tgcagaattc ggcttactat agggcacgcg tggtcgacgg cccgggctgg     120
tatccatatt ccatttttat attatttatt tttaatataa ttattatttt tttaattatt     180 ttaaaattt taaatttcca ttaacctaat tttttctaa ataaattatt catataaata       240
aagaaattaa aaatactaac attttaaaaa tctcaaaaat tcgttattcg aaaattattg     300
ttttcctgaa atatatatat gaaaaatact ttaaaatttt atcaaataat atttaaaata     360
tataaaataa agttcatttt gtcaacataa atttagaaat aaaaaactaa aaattaatat    420
gaaaaaaatt gataaccaaa ctaaactaaa ttataattaa aagttcaaaa aattaaaaaa    480
atcccgattg aaccagtatc acccctaaat tagatgaggc catatttaac atattagaaa    540
atgaaactct agaaaaatat ataaaagtaa atttattggc gagagattag acaaagtcaa    600
```

-continued

```
tgcacccctc aatgaataga tattattccc aatgaaagtt tccgtttcc acctcctacc      660
caaaaactcc aaagtctcca gaagacgcgc ctgaatcgtg actgggtagc cggggtacat     720
actacaaccc taaatgcttt atagcgcata gatcatgggt ttagctttgg atcccataaa     780
gtacaaatac tgaggttctt tagtgaatga tcatgcatgg acacatgatg tctctttta     840
ggcatttgac aaactcgtca tttttcata caatttcttt ggtcaattaa attttccatt      900
aaattaggaa accgccctcc aaaattatan tggtaacggt ggaaggntta tccaanttcg     960
accattcgaa ccacttttaa aaaattagaa agttataatt ttttttcaa aaaaactata    1020
atacctctct agttttagct aattaaatta ttattatttt attatttat tgttattaaa    1080
agtgtaactt gcactcaact attagtaagt ttacgtttg atcacttaat ttcagaaagt    1140
taaaaaatgg tctttgaact attcgaaaat tttcatttaa gttactggaa tatttaaaag   1200
tttttattta agtcaccggg ctattaagtt ttttttaaa aattcgatta gcaagttcca   1260
agctacgatt cgataagtga tacaatggat ttatacttat tgacaaatag aatatacatt   1320
aggtccaagt tgatattacg gtcagtgttg aaaatcgaaa aaaatatttt ggattttgat   1380
tcataaattt atgacttcaa agctggttca tgaaaagaa ctaaagtgta ggagggaagg    1440
aaaaaaatat cttttgattg gcacaaacag tgcgaacaaa gaagaccaca caataacaat   1500
tttaacaata tactaattta aatgaaaaat tttcaataat ttaataagtt aaccgaggaa   1560
aacttactaa gagttagtta ccccctgtta aaataacttt catgaagtaa tagaaacttt   1620
tagtacgtat catcttatat agaacaattc tattttcagg aaagtcaaag aaaattgtat   1680
tgtagaaaat ggcgaatttt ttcaccttca gtcctttccc tgatcggcgc ttgtgaaaaa   1740
cgaaaaacct gagtctgatt ggctgactga aaatgaactt atcatcacca ttcactatta   1800
ccaacttcaa atgatagggg aattaactgg taaagtgtaa ctccaccgat ggttgaggtg   1860
gttggctgga gttaaatgag attttttag ttttgtttca agtggcttca attgcaagca    1920
attaggagac tgcgctggaa tacccctcg ctcaaccttc cgccattgtt atggtttaat    1980
taaacattat gtttccatcc atctatattt atatccatta aaacaagtcg ttgagcaaat   2040
aatggatact ggataccatc atatctatga ttaaaatttt gcatgtgccc ttttaatgta   2100
tagcttaagc cttaattatc ctccaaattt gtactctttc accacttaat tagctacgta   2160
cggtacttag cgttgcttgt catcttctgt actacaaact ctttctcatt ttgtataaat   2220
agctatacac tttttctctc ctcaaatcaa taaggttagg tcagccaatt gtttgagcta   2280
gctagctctt actcaaatgg caaccaaaac gatgatgttg caaatatttc cacttttctt   2340
cttttttgttc agtgtctgca actccatttt ccttggtgct aatggagatg acaatggtgg   2400
ttggcaaact gcccatgcca ccttctacgg tggtgctgat gctaccggca caatgggtga   2460
gtttcaaact ttcaaaccat tacggcatta cctacataaa aatctctagg ctatgttctt   2520
aatttgtgat gttctctata gggggagctt gtggttatgg aaacctgtac agtcaaagcc   2580
gaattccagc acactggcgg ccgttactag tgga                               2614
```

COTTON EXPANSIN PROMOTER SEQUENCE

RELATED APPLICATIONS

This application is a continuation-in-part of U.S. application Ser. No. 60/034,914 filed Jan. 7, 1997.

BACKGROUND OF THE INVENTION

1. Technical Field

This invention relates to a cotton expansin promoter encoding sequence, and its use in contructs useful in modifying cotton fiber phenotypes.

This invention particularly relates to methods of using in vitro constructed DNA transcription or expression cassettes capable of directing fiber-tissue transcription of a DNA sequence of interest in cotton to produce fiber cells having an altered phenotype, and to methods of providing for or modifying various characteristics of cotton fiber as well as the modified cotton fibers produced by the method.

2. Background

In general, genetic engineering techniques have been directed to modifying the phenotype of individual prokaryotic and eukaryotic cells, especially in culture. Plant cells have proven more intransigent than other eukaryotic cells, due not only to a lack of suitable vector systems but also as a result of the different goals involved. For many applications, it is desirable to be able to control gene expression at a particular stage in the growth of a plant or in a particular plant part. For this purpose, regulatory sequences are required which afford the desired initiation of transcription in the appropriate cell types and/or at the appropriate time in the plant's development without having serious detrimental effects on plant development and productivity.

It is therefore of interest to be able to isolate sequences which can be used to provide the desired regulation of transcription in a plant cell during the growing cycle of the host plant.

One aspect of this interest is the ability to change the phenotype of particular cell types, such as differentiated epidermal cells that originate in fiber tissue, i.e. cotton fiber cells, so as to provide for altered or improved aspects of the mature cell type. Cotton is a plant of great commercial significance. In addition to the use of cotton fiber in the production of textiles, other uses of cotton include food preparation with cotton seed oil and animal feed derived from cotton seed husks.

Despite the importance of cotton as a crop, the breeding and genetic engineering of cotton fiber phenotypes has taken place at a relatively slow rate because of the absence of reliable promoters for use in selectively effecting changes in the phenotype of the fiber. In order to effect the desired phenotypic changes, transcription initiation regions capable of initiating transcription in fiber cells during development are desired. Thus, an important goal of cotton bioengineering research is the acquisition of a reliable promoter which would permit expression of a protein selectively in cotton fiber to affect such qualities as fiber strength, length, color and dyability.

Relevant Literature

Cotton fiber-specific promoters are discussed in PCT publications WO 94/12014 and WO 95/08914, and John and Crow, Proc. Natl. Acad. Sci. USA, 89:5769–5773, 1992. cDNA clones that are preferentially expressed in cotton fiber have been isolated. One of the clones isolated corresponds to mRNA and protein that are highest during the late primary cell wall and early secondary cell wall synthesis stages. John and Crow, supra.

Agrobacterium-mediated cotton transformation is described in Umbeck, U.S. Pat. Nos. 5,004,863 and 5,159,135 and cotton transformation by particle bombardment is reported in WO 92/15675, published Sep. 17, 1992. Transformation of Brassica has been described by Radke et al. (Theor. Appl. Genet. (1988) 75;685–694; Plant Cell Reports (1992) 11:499–505.

SUMMARY OF THE INVENTION

The invention provides a cotton (*Gossypium hirsutum*) promoter region from an expansin gene expressed in developing fiber. Novel DNA promoter sequences are supplied, and methods for their use are described for directing transcription of a gene of interest in cotton fiber using the promoter region from an expansin gene which is expressed in cotton fiber.

In efforts to identify genes critical to fiber development, we have initiated a program sequencing randomly selected cDNA clones derived from a library prepared from mRNA harvested from fibers at the stage in which secondary wall synthesis approaches its maximum rate (approximately 21 dpa).

We have characterized a cotton (*Gossypium hirsutum*) cDNA clone which is a homolog of the expansin gene. The sequences of this cDNA clone is homologous to that of other expansin encoding sequences The 5' genomic promoter region from this gene has been sequenced for approximately 2200 base pairs.

Thus, the application provides sequences and methods of use relating to modification of phenotype in cotton fiber using a promoter of the cotton expansin gene.

DETAILED DESCRIPTION OF THE INVENTION

Figure 1A:
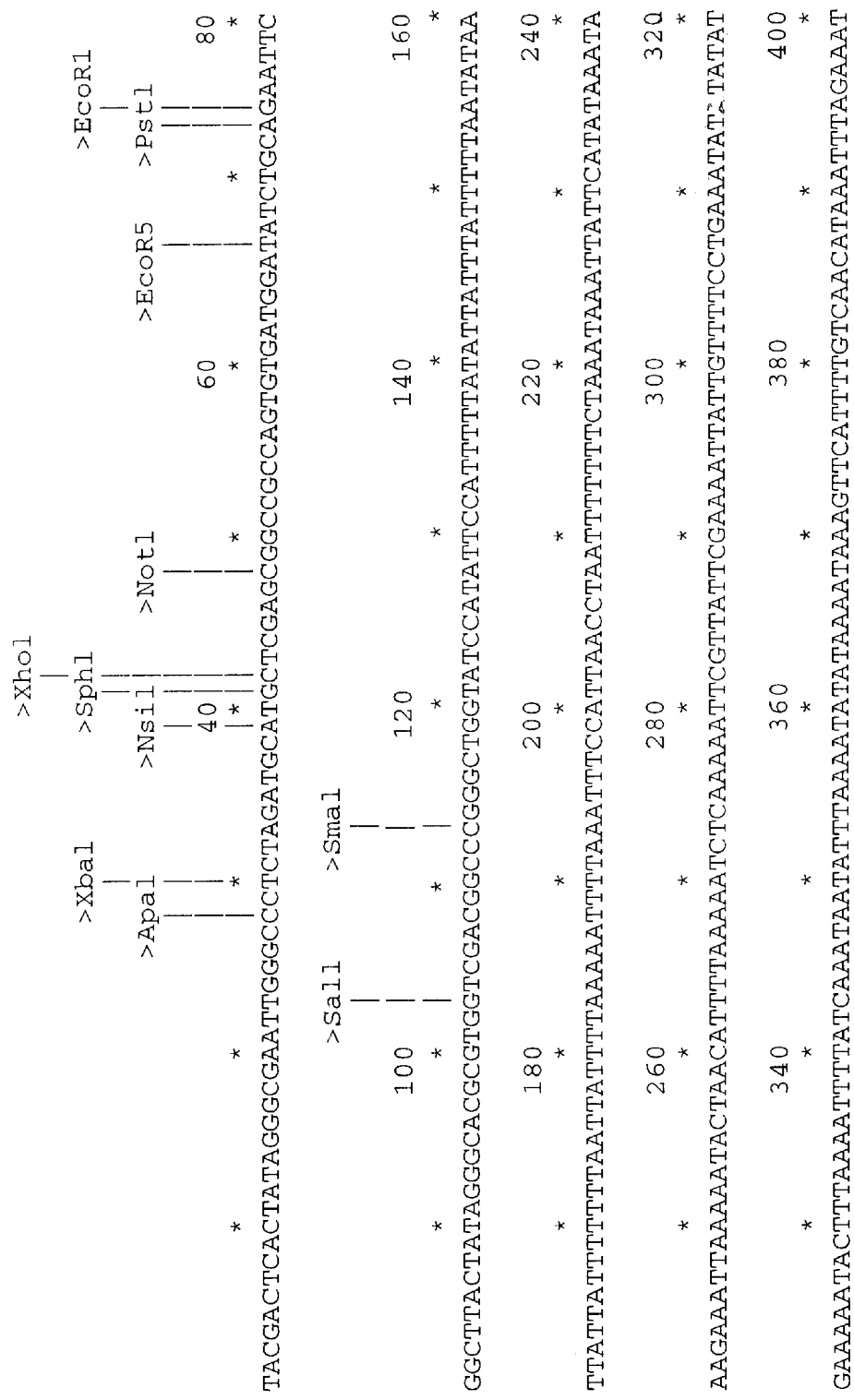
FIG. 1. Nucleic acid sequences to approximately 2200 bases of the promoter region 5' to the encoding sequences to the cotton fiber expansin gene (SEQ ID NO:1).

In accordance with the subject invention, novel constructs and methods are described, which may be used for transcription of a nucleotide sequence of interest in cells of a plant host, preferentially in cotton fiber cells to produce cotton fiber having an altered phenotype.

Cotton fiber is a differentiated single epidermal cell of the outer integument of the ovule. It has four distinct growth phases; initiation, elongation (primary cell wall synthesis), secondary cell wall synthesis, and maturation. Initiation of fiber development appears to be triggered by hormones. The primary cell wall is laid down during the elongation phase, lasting up to 25 days postanthesis (DPA). Synthesis of the secondary wall commences prior to the cessation of the elongation phase and continues to approximately 40 DPA, forming a wall of almost pure cellulose.

The constructs for use in such cells may include several forms, depending upon the intended use of the construct. Thus, the constructs include vectors, transcriptional cassettes, expression cassettes and plasmids. The transcriptional and translational initiation region (also sometimes referred to as a "promoter,") contains the transcriptional and translational functional elements and the initiation control region derived from or obtainable from the expansin gene (FIG. 1).

In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

A transcriptional cassette for transcription of a nucleotide sequence of interest in cotton fiber will include in the direction of transcription, the cotton fiber transcriptional initiation region from expansin, a DNA sequence of interest, and a transcriptional termination region functional in the plant cell. When the cassette provides for the transcription and translation of a DNA sequence of interest it is considered an expression cassette. One or more introns may be also be present.

Other sequences may also be present, including those encoding transit peptides and secretory leader sequences as desired.

Downstream from, and under the regulatory control of, the expansin transcriptional/translational initiation control region is preferably a nucleotide sequence of interest which provides for modification of the phenotype of fiber. The nucleotide sequence may be any open reading frame encoding a polypeptide of interest, for example, an enzyme, or a sequence complementary to a genomic sequence, where the genomic sequence may be an open reading frame, an intron, a noncoding leader sequence, or any other sequence where the complementary sequence inhibits transcription, messenger RNA processing, for example, splicing, or translation. The nucleotide sequences of this invention may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest. Phenotypic modification can be achieved by modulating production either of an endogenous transcription or translation product, for example as to the amount, relative distribution, or the like, or an exogenous transcription or translation product, for example to provide for a novel function or products in a transgenic host cell or tissue. Of particular interest are DNA sequences encoding expression products associated with the development of plant fiber, including genes involved in metabolism of cytokinins, auxins, ethylene, abscissic acid, and the like. Methods and compositions for modulating cytokinin expression are described in U.S. Pat. No. 5,177,307, which disclosure is hereby incorporated by reference. Alternatively, various genes, from sources including other eukaryotic or prokaryotic cells, including bacteria, such as those from *Agrobacterium tumefaciens* T-DNA auxin and cytokinin biosynthetic gene products, for example, and mammals, for example interferons, may be used.

The termination region which is employed in the expression cassette will be primarily one of convenience, since the termination regions appear to be relatively interchangeable. The termination region may be native with the transcriptional initiation region, may be native with the DNA sequence of interest, may be derived from another source. The termination region may be naturally occurring, or wholly or partially synthetic. Convenient termination regions are available from the Ti-plasmid of *A. tumefaciens*, such as the octopine synthase and nopaline synthase termination regions. In some embodiments, it may be desired to use the 3' termination region native to the cotton fiber transcription initiation region used in a particular construct.

As described herein, in some instances additional nucleotide sequences will be present in the constructs to provide for targeting of a particular gene product to specific cellular locations.

A variety of techniques are available and known to those skilled in the art for introduction of constructs into a plant cell host. These techniques include transfection with DNA employing *A. tumefaciens* or *A. rhizogenes* as the transfecting agent, protoplast fusion, injection, electroporation, particle acceleration, etc. For transformation with Agrobacterium, plasmids can be prepared in *E. coli* which contain DNA homologous with the Ti-plasmid, particularly T-DNA. The plasmid may or may not be capable of replication in Agrobacterium, that is, it may or may not have a broad spectrum prokaryotic replication system such as does, for example, pRK290, depending in part upon whether the transcription cassette is to be integrated into the Ti-plasmid or to be retained on an independent plasmid. The Agrobacterium host will contain a plasmid having the vir genes necessary for transfer of the T-DNA to the plant cell and may or may not have the complete T-DNA. At least the right border and frequently both the right and left borders of the T-DNA of the Ti- or Ri-plasmids will be joined as flanking regions to the transcription construct. The use of T-DNA for transformation of plant cells has received extensive study and is amply described in EPA Serial No. 120,516, Hoekema, In: The Binary Plant Vector System Offsetdrukkerij Kanters B. V., Alblasserdam, 1985, Chapter V, Knauf, et al., Genetic Analysis of Host Range Expression by Agrobacterium, In: Molecular Genetics of the Bacteria-Plant Interaction, Puhler, A. ed., Springer-Verlag, N.Y., 1983, p. 245, and An, et al., *EMBO J.* (1985) 4:277–284.

For infection, particle acceleration and electroporation, a disarmed Ti-plasmid lacking particularly the tumor genes found in the T-DNA region) may be introduced into the plant cell. By means of a helper plasmid, the construct may be transferred to the *A. tumefaciens* and the resulting transfected organism used for transfecting a plant cell; explants may be cultivated with transformed *A. tumefaciens* or *A. rhizogenes* to allow for transfer of the transcription cassette to the plant cells. Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated. Transgenic plant cells are then placed in an appropriate selective medium for selection of transgenic cells which are then grown to callus, shoots grown and plantlets generated from the shoot by growing in rooting medium.

To confirm the presence of the transgenes in transgenic cells and plants, a Southern blot analysis can be performed using methods known to those skilled in the art. Expression products of the transgenes can be detected in any of a variety of ways, depending upon the nature of the product, and include immune assay, enzyme assay or visual inspection, for example to detect pigment formation in the appropriate plant part or cells. Once transgenic plants have been obtained, they may be grown to produce fiber having the desired phenotype. The fibers may be harvested, and/or the seed collected. The seed may serve as a source for growing additional plants having the desired characteristics. The terms transgenic plants and transgenic cells include plants and cells derived from either transgenic plants or transgenic cells.

The various sequences provided herein may be used as molecular probes for the isolation of other sequences which may be useful in the present invention, for example, to obtain related transcriptional initiation regions from the same or different plant sources. Related transcriptional initiation regions obtainable from the sequences provided in this invention will show at least about 60% homology, and more preferred regions will demonstrate an even greater percentage of homology with the probes.

Of particular importance is the ability to obtain related transcription initiation control regions having the timing and tissue parameters described herein. Thus, by employing the techniques described in this application, and other techniques known in the art (such as Maniatis, et al., *Molecular Cloning,—A Laboratory Manual* (Cold Spring Harbor, N.Y.) 1982), other encoding regions or transcription initiation regions of expansin as described in this invention may be determined. The constructs can also be used in conjunction with plant regeneration systems to obtain plant cells and plants; thus, the constructs may be used to modify the phenotype of fiber cells, to provide cotton fibers which are colored as the result of genetic engineering to heretofor unavailable hues and/or intensities.

Various varieties and lines of cotton may find use in the described methods. Cultivated cotton species include *Gossypium hirsutum* and *G. babadense* (extra-long stable, or Pima cotton), which evolved in the New World, and the Old World crops *G. herbaceum* and *G. arboreum*.

EXAMPLES

The following examples are offered by way of illustration and not by limitation.

Example 1 cDNA Libraries

An unamplified cDNA library was used to prepare the Lambda Uni-Zap vector (Stratagene, LaJolla, Calif.) using cDNA derived from polyA+ mRNA prepared from fibers of *Gossypium hirsutum* Acala SJ-2 harvested at 21 DPA, the time at which secondary wall expansion is approaching a maximal rate. Approximately 250 plaques were randomly selected from the cDNA library, phages purified and plasmids excised from the phage vector and transformed.

The resulting clones/inserts were size screened on 0.8% agarose gels (DNA inserts below 600 bp were excluded).

Example 2

Isolation and Sequencing of cDNA Clones

Plasmid DNA inserts were randomly sequenced using an Applied Biosystems (Foster City, Calif.) Model 373A DNA sequencer.

Example 3

Northern and Southern Analyses

Cotton plants (*G. hirsutum* cv. Coker 130) were grown in the greenhouse and tissues harvested at the appropriate times indicated and frozen in liquid $N_2$. Total cotton RNA and cotton genomic DNA was prepared and subjected to Northern and Southern analyses as described previously.

Example 4

Identification, Differential Expression and Genomic Analysis of Cotton Expansin Genes During the course of screening and sequencing random cDNA clones from a cotton fiber specific cDNA library, it was discovered that one cDNA clone was very active during primary cell wall development and had homology to the protein encoded by the expansin genes.

This clone was then utilized as a probe for Northern blot analysis to determine the differential expression in cotton tissues and developing cotton fiber. The expansin gene encodes a mRNA which is expressed at high levels in developing fiber, beginning at approximately day 1 through primary cell wall development at approximately day 20 post anthesis.

Example 5

Genomic DNA cDNA for the expansin clone was used to probe for genomic clones. Full length genomic DNA was obtained from a library made using the lambda dash 2 vector from Stratagene™, which was used to construct a genomic DNA library from cotton variety Coker 130 (*Gossypium hirsutum* cv. coker 130), using DNA obtained from germinating seedlings.

The cotton genomic library was probed with a expansin probe and genomic phage candidates were identified and purified. FIG. 1 provides an approximately 2200 base pair sequence of the expansin promoter region which is immediately 5' to the expansin encoding region. The start of the expansin enzyme encoding region is at the ATG at base number 2297, and the genomic clone begins at base number 122 of FIG. 1.

Example 6

Cotton Transformation

Construct Preparation

Promoter constructs comprising the expansin promoter sequences linked to a gene of interest and other genetic elements of interest can be prepared in any of a number of ways known to the art, such as by ligation.

Explant Preparation

Coker 315 seeds are surface disinfected by placing in 50% Clorox (2.5% sodium hypochlorite solution) for 20 minutes and rinsing 3 times in sterile distilled water. Following surface sterilization, seeds are germinated in 25×150 sterile tubes containing 25 mls ½ x MS salts: ½ x B5 vitamins: 1.5% glucose: 0.3% gelrite. Seedlings are germinated in the dark at 28° C. for 7 days. On the seventh day seedlings are placed in the light at 28±2° C.

Cocultivation and Plant Regeneration

Single colonies of *A. tumefaciens* strain 2760 containing binary plasmids pCGN2917 and pCGN2926 are transferred to 5 ml of MG/L broth and grown overnight at 30° C. Bacteria cultures are diluted to $1\times10^8$ cells/ml with MG/L just prior to cocultivation. Hypocotyls are excised from eight day old seedlings, cut into 0.5–0.7 cm sections and placed onto tobacco feeder plates (Horsch et al. 1985). Feeder plates are prepared one day before use by plating 1.0 ml tobacco suspension culture onto a petri plate containing Callus Initiation Medium CIM without antibiotics (MS salts: B5 vitamins: 3% glucose: 0.1 mg/L 2,4-D: 0.1 mg/L kinetin: 0.3% gelrite, pH adjusted to 5.8 prior to autoclaving). A sterile filter paper disc (Whatman #1) was placed on top of the feeder cells prior to use. After all sections are prepared, each section was dipped into an *A. tumefaciens* culture, blotted on sterile paper towels and returned to the tobacco feeder plates.

Following two days of cocultivation on the feeder plates, hypocotyl sections are placed on fresh Callus Initiation Medium containing 75 mg/L kanamycin and 500 mg/L carbenicillin. Tissue is incubated at 28±2° C., 30 uE 16:8 light:dark period for 4 weeks. At four weeks the entire explant is transferred to fresh callus initiation medium containing antibiotics. After two weeks on the second pass, the callus is removed from the explants and split between Callus Initiation Medium and Regeneration Medium (MS salts: 40 mM $KNO_3$: 10 mM $NH_4Cl$:B5 vitamins:3% glucose:0.3% gelrite:400 mg/L carb: 75 mg/L kanamycin).

Embryogenic callus is identified 2–6 months following initiation and was subcultured onto fresh regeneration medium. Embryos are selected for germination, placed in static liquid Embryo Pulsing Medium (Stewart and Hsu medium: 0.01 mg/l NAA: 0.01 mg/L kinetin: 0.2 mg/L GA3) and incubated overnight at 30° C. The embryos are blotted on paper towels and placed into Magenta boxes containing 40 mls of Stewart and Hsu medium solidified with Gelrite. Germinating embryos are maintained at 28±2° C. 50 uE $m^{-2}s^{-1}$ 16:8 photoperiod. Rooted plantlets are transferred to soil and established in the greenhouse.

Cotton growth conditions in growth chambers are as follows: 16 hour photoperiod, temperature of approximately 80–85°, light intensity of approximately 500 μEinsteins. Cotton growth conditions in greenhouses are as follows: 14–16 hour photoperiod with light intensity of at least 400 μEinsteins, day temperature 90–95° F., night temperature 70–75° F., relative humidity to approximately 80%.

Plant Analysis

Flowers from greenhouse grown Tl plants are tagged at anthesis in the greenhouse. Squares (cotton flower buds), flowers, bolls etc. are harvested from these plants at various stages of development and assayed for observable phenotype or tested for enzyme activity.

The above results demonstrate how the expansin cDNA may be used to alter the phenotype of a transgenic plant cell, and how the promoter may be used to modify transgenic cotton fiber cells.

All publications and patent applications cited in this specification are herein incorporated by reference as if each individual publication or patent application are specifically and individually indicated to be incorporated by reference.

Although the foregoing invention has been described in some detail, by way of illustration and example for purposes of clarity and understanding, it will be readily apparent to those of ordinary skill in the art that certain changes and modifications may be made thereto, without departing from the spirit or scope of the appended claims.

What is claimed is:

1. An isolated DNA sequence comprising the sequence of SEQ ID NO: 1.

2. A recombinant DNA construct comprising the DNA sequence of claim 1.

3. A plant cell comprising the DNA construct of claim 2.

4. A plant comprising the plant cell of claim 3.

* * * * *